United States Patent
Watson, Jr. et al.

(10) Patent No.: US 6,436,961 B1
(45) Date of Patent: Aug. 20, 2002

(54) PHARMACEUTICAL AGENTS FOR THE TREATMENT OF EMESIS

(75) Inventors: Harry A. Watson, Jr., Groton; William M. Snyder, New London, both of CT (US); Glenn E. Wilcox, Cranston, RI (US)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 08/529,891

(22) Filed: Sep. 18, 1995

Related U.S. Application Data

(63) Continuation of application No. PCT/IB94/00059, filed on Apr. 6, 1994, and a continuation of application No. 08/068,471, filed on May 28, 1993, now abandoned.

(51) Int. Cl.$^7$ .................. A61K 31/445; A61K 31/165; C07F 213/00; C07F 9/80
(52) U.S. Cl. .................. 514/329; 514/872; 514/318; 514/319; 514/323; 514/324; 514/326; 546/2; 546/10; 546/13
(58) Field of Search ................ 546/2, 10, 13; 514/329, 872, 318, 319, 323, 324, 326

(56) References Cited

U.S. PATENT DOCUMENTS

| | | | |
|---|---|---|---|
| 1,139,778 A | 5/1915 | Landreth | 210/751 |
| 2,029,958 A | 2/1936 | Urbain | 210/763 |
| 3,017,347 A | 1/1962 | Kratz | 210/63 |
| 3,442,802 A | 5/1969 | Hamilton et al. | 210/63 |
| 3,487,016 A | 12/1969 | Zeff | 210/18 |
| 3,586,623 A | 6/1971 | Kuhn | 210/63 |
| 3,664,951 A | 5/1972 | Armstrong | 210/767 |
| 3,817,862 A | 6/1974 | Hoke | 216/759 |
| 4,007,118 A | 2/1977 | Ciambrone | 210/63 |
| 4,029,557 A | 6/1977 | Christensen et al. | 204/149 |
| 4,072,596 A | 2/1978 | Moeglich | 204/241 |
| 4,073,873 A | 2/1978 | Caldwell et al. | 423/499 |
| 4,131,526 A | 12/1978 | Moeglich | 264/149 |
| 4,179,347 A | 12/1979 | Krause et al. | 204/149 |
| 4,218,315 A | 8/1980 | Hartkorn | 210/26 |
| 4,292,175 A | 9/1981 | Krause et al. | 210/192 |
| 4,297,333 A | 10/1981 | Crawford et al. | 423/241 |
| 4,402,836 A | 9/1983 | Fochtman et al. | 210/748 |
| 4,445,990 A | 5/1984 | Kim et al. | 204/151 |
| 4,472,281 A | 9/1984 | Kerridge | 210/668 |
| 4,534,867 A | 8/1985 | Kreusch et al. | 210/722 |
| 4,549,969 A | 10/1985 | Gerlach et al. | 210/759 |
| 4,676,878 A | 6/1987 | Chez | 204/101 |
| 4,696,749 A | 9/1987 | Habermann et al. | 210/721 |
| 4,732,688 A | 3/1988 | Bryan et al. | 210/753 |
| 4,761,208 A | 8/1988 | Gram et al. | 204/95 |
| 4,764,286 A | 8/1988 | Bon et al. | 210/757 |
| 4,861,484 A | 8/1989 | Lichtin et al. | 210/138 |
| 4,906,387 A | 3/1990 | Pisani | 210/748 |
| 4,954,230 A | 9/1990 | Kirsch | 204/149 |
| 5,094,734 A | 3/1992 | Torrado | 204/254 |
| 5,108,563 A | 4/1992 | Cook | 204/149 |
| 5,154,836 A | 10/1992 | Clough | 210/747 |
| 5,167,777 A | 12/1992 | Kaczur et al. | 204/129 |
| 5,190,659 A | 3/1993 | Wang et al. | 710/663 |
| 5,204,008 A | 4/1993 | Diehl et al. | 210/759 |
| 5,207,925 A | 5/1993 | Steiner et al. | 210/746 |
| 5,232,604 A | 8/1993 | Swallow et al. | 210/759 |
| 5,232,929 A | * 8/1993 | Desai et al. | 514/314 |
| 5,288,373 A | 2/1994 | Yang | 204/131 |
| 5,324,438 A | 6/1994 | McPhee et al. | 210/748 |
| 5,352,370 A | 10/1994 | Hayden | 210/763 |
| 5,364,508 A | 11/1994 | Weres et al. | 204/128 |
| 5,364,509 A | 11/1994 | Dietrich | 204/141 |
| 5,376,240 A | 12/1994 | Kaczur et al. | 204/128 |
| 5,547,964 A | * 8/1996 | Hagan et al. | 514/329 |

FOREIGN PATENT DOCUMENTS

| | | |
|---|---|---|
| EP | 0533280 | 3/1993 |
| WO | WO9118878 | 12/1991 |
| WO | WO 9217449 | 10/1992 |

* cited by examiner

Primary Examiner—Russell Travers
(74) Attorney, Agent, or Firm—Peter C. Richardson; Paul H. Ginsburg; Karen DeBenedictis

(57) ABSTRACT

The present invention relates to a novel process for preparing and resolving 3-amino-2-phenylpiperidine and for synthesizing from the enantiomers of such compound certain pharmaceutically active substituted 2-phenyl-3-benzylaminopiperidines. The substituted 2-phenyl-3-benzylaminopiperidines that can be prepared by the processes of this invention are substance P receptor antagonists and are useful in the treatment and prevention of inflammatory and central nervous system disorders, as well as several other disorders.

7 Claims, No Drawings

PHARMACEUTICAL AGENTS FOR THE TREATMENT OF EMESIS

This application is a continuation of International application No. PCT/IB94/00059, filed Apr. 6, 1994, which designates the United States and is a continuation of U.S. Ser. No. 08/068,471, filed on May 28, 1993.

BACKGROUND OF THE INVENTION

The present invention relates to a novel process for preparing and resolving 3-amino-2-phenylpiperidine and for synthesizing from the enantiomers of such compound certain pharmaceutically active substituted 2-phenyl-3-benzylaminopiperidines. The substituted 2-phenyl3-benzylaminopiperidines that can be prepared by the processes of this invention are substance P receptor antagonists and are useful in the treatment and prevention of inflammatory, gastrointestinal and central nervous system disorders, as well as several other disorders.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals and possesses the characteristic amino acid sequence illustrated by D. F. Veber et al. in U.S. Pat. No. 4,680,283. The wide involvement of substance P and other tachykinins in the pathophysiology of numerous diseases has been amply demonstrated in the art. For instance, substance P has been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

The substituted 2-phenyl-3-benzylaminopiperidines that can be prepared by the processes of this invention, as well as methods for preparing such compounds, are referred to in U.S. patent application Ser. No. 07/724,268, which was filed on Jul. 1, 1990 and World Patent Application PCT/US92/03571, which was published on Jan. 7, 1993 (WO 93/00331). Methods for preparing such compounds are also referred to in U.S. patent application Ser. No. 07/800,667, which was filed on Nov. 27,1991 and World Patent Application PCT/US92/00065 which was published on Oct. 15, 1992 (WO 92,17449).

SUMMARY OF THE INVENTION

The present invention relates to a process for resolving racemic or optically enriched 3-amino-2-phenylpiperidine, comprising reacting a starting material which is racemic 2-phenyl-3-aminopiperidine or an optically active mixture of (2R,3R)-3-amino-2-phenylpiperidine and (2S,3S)-3-amino-2-phenylpiperidine with L-(+)-mandelic acid or D-(−)-mandelic acid.

This invention also relates to a process for preparing a compound of the formula

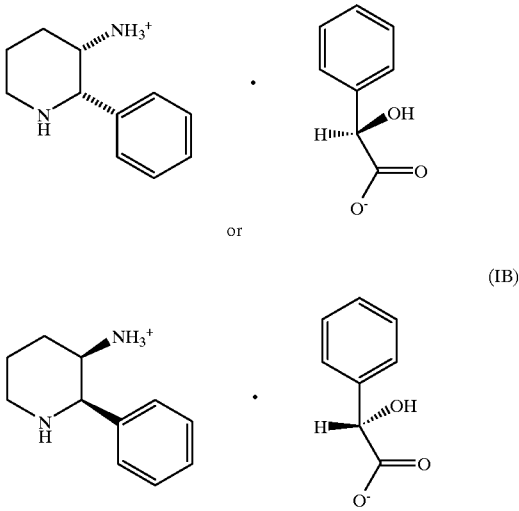

comprising reacting L-(+)-mandelic acid with either racemic 3-amino-2-phenylpiperidine or an optically active mixture of (2R,3R)-3-amino-2-phenylpiperidine and (2S,3S)-3-amino-2-phenylpiperidine to form a compound of the formula IA, or reacting D-(−)-mandelic acid with either racemic 3-amino-2-phenylpiperidine or an optically active mixture of (2R,3R)-3-amino-2-phenylpiperidine and (2S,3S)-3-amino-2-phenylpiperidine to form a compound of the formula IB.

This invention also relates to the above process, wherein the compound of formula IA or IB formed is neutralized to form, respectively, (2S,3S)-3-amino-2-phenylpiperidine or (2R,3R)-3-amino-2-phenylpiperidine.

This invention also relates to the above process wherein the (2S,3S)-3-amino-2-piperidine or (2R,3R)-3-amino-2-piperidine formed is reacted with either (a) a compound of the formula

$$R^1CX,$$

wherein X is a leaving group (e.g., chloro, bromo, iodo or imidazole) and $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said ($C_3$–$C_7$) cycloalkyl may optionally be substituted with one or two substituents, said substituents being independently selected from chloro, fluoro, bromo, iodo, nitro, ($C_1$–$C_{10}$) alkyl optionally substituted from one to three fluoro groups, ($C_1$–$C_{10}$) alkoxy optionally substituted with from one to three fluoro groups, amino,

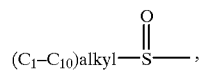

$$(C_1\text{–}C_{10})\text{alkyl}-\overset{\overset{\displaystyle O}{\|}}{S}-,$$

($C_1$–$C_{10}$)alkyl-S—, ($C_1$–$C_{10}$)alkyl-$SO_2$—, phenyl, phenoxy, ($C_1$–$C_{10}$)alkyl-$SO_2NH$—, ($C_1$–$C_{10}$)alkyl-$SO_2NH$—($C_1$–$C_{10}$)alkyl-, ($C_1$–$C_{10}$)alkylamino-di($C_1$–$C_{10}$)alkyl-, cyano, hydroxy, cycloalkoxy having 3 to 7 carbon atoms, $(C_1-C_6)$alkylamino, $(C_1-C_6)$dialkylamino,

and

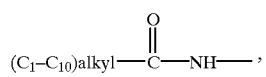

wherein the nitrogen atoms of said amino and $(C_1-C_6)$ alkylamino groups may optionally be protected with an appropriate protecting group; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, $(C_1-C_{10})$alkyl optionally substituted with from one to three fluoro groups and $(C_1-C_{10})$ alkoxy optionally substituted with from one to three fluoro groups, followed by treatment of the resulting amide with a reducing agent, (b) a compound of the formula $R^1CHO$, wherein $R^1$ is defined as above, in the presence of a reducing agent, or (c) a compound of the formula $R^1CH_2X$, wherein $R^1$ is defined as above and X is a leaving group (e.g., chloro, bromo, iodo, mesylate or tosylate), to form respectively, a compound of the formula

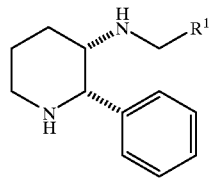

(VA)

or

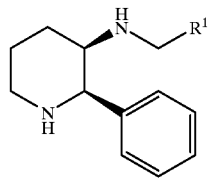

(VB)

wherein $R^1$ is defined as above.

This invention also relates to the novel optically active salts of formulae IA and IB.

The term "halo", as used herein, unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

The term "alkoxy", as used herein, includes O-alkyl groups wherein "alkyl" is defined as above.

The term "one or more substituents," as used herein, includes from one to the maximum number of substituents possible based on the number of available bonding sites.

Preferred embodiments of this invention are the resolution processes referred to above wherein the resolving agent is L-(+)-mandelic acid and the solvent is acetonitrile.

Other preferred embodiments of this invention are compounds of the formula VA or VB wherein $R^1$ is phenyl or substituted phenyl. More preferred are compounds of the formula VA wherein $R^1$ is phenyl substituted with from 1 to 3 substituents independently selected from one to three fluorine atoms and $(C_1-C_{16})$alkoxy optionally substituted with from one to three fluorine atoms.

DETAILED DESCRIPTION OF THE INVENTION

The processes of this invention are depicted in the following reaction scheme. Unless otherwise indicated, in the reaction scheme and discussion that follow, $R^1$ is defined as above.

Scheme 1

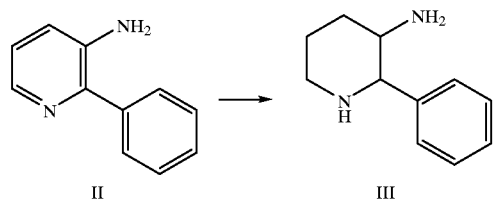

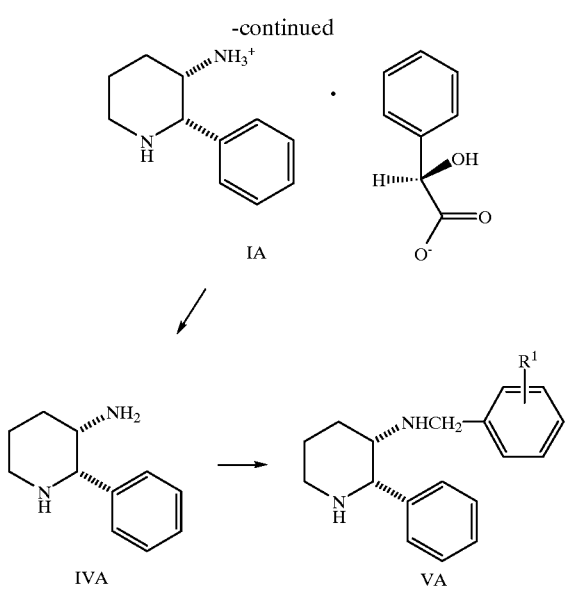

IA

IVA → VA

Referring to scheme 1, the pyridine of formula II is reduced to form the corresponding piperidine of formula III. This reduction is generally accomplished using either sodium in alcohol, lithium aluminum hydride/aluminum trichloride, electrolytic reduction or hydrogen in the presence of a metal catalyst. The reduction with sodium is generally conducted in a boiling alcohol, preferably butanol, at a temperature from about 20° C. to about the reflux temperature of the solvent, preferably at about 120° C. The reduction with lithium aluminum hydride/aluminum trichloride is usually carried out in ether, tetrahydrofuran (THF) or dimethoxyethane, preferably ether, at a temperature from about 25° C. to about 100° C., preferably at about room temperature. The electrolytic reduction is conducted, preferably, at room temperature, but temperatures from about 10° C. to about 60° C. are also suitable.

Hydrogenation in the presence of a metal catalyst is the preferred method of reduction. Suitable hydrogenation catalysts include palladium, platinum, nickel and rhodium. The preferred catalyst for hydrogenation is platinum on carbon. The reaction temperature may range from about 10° C. to about 50° C., with about 25° C. being preferred. The hydrogenation is generally carried out at a pressure from about 1.5 to about 4 atmospheres, preferably at about 3.0 atmospheres.

The resolution of 3-amino-2-phenylpiperidine is carried out by reacting racemic 3-amino-2-phenylpiperidine or an optically active mixture of (2R,3R)-3-amino-2-phenylpiperidine and (2S,3S)-3amino-2-phenylpiperidine with L-(+)-mandelic acid or D-(−)-mandelic acid in an appropriate solvent. An appropriate solvent is any solvent capable of dissolving the reactants and selectively dissolving one of the two optically active salts formed (i.e. the compounds of formulae IA and IB), while causing the other to precipitate out of solution. Examples of appropriate solvents are acetonitrile, ethyl acetate, 2-propanol and methyl ethyl ketone. The resolution may be carried out at temperatures ranging from about 20° C. to about 120° C., and is preferably carried out at about room temperature.

When L-(+)-mandelic acid is used as the resolving agent, as described above, the L-(+)-mandelic acid salt of (2S,3S)-3amino-2-phenyl piperidine (IVA) precipitates out of solution and can be physically separated and purified by methods well known to those skilled in the art. The L-(+)-mandelate salt of the opposite enantiomer, (2R,3R)-3-amino-2-phenylpiperidine (IVB), remains in solution. When D-(−)-mandelic acid is used as the resolving agent, the D-(−)-mandelic acid salt of (2R,3R)-3-amino-2 -phenylpiperidine precipitates out of solution, while the D-(−)-mandelic acid salt of (2S,3S)-3-amino-2-phenylpiperidine remains in solution.

Neutralization of the mandelate salts of (2S,3S)-3-amino-2-phenylpiperidine and (2R,3R)-3-amino-2-phenylpiperidine to form the corresponding optically active free amines may be accomplished using methods well known in the art. For example, such neutralization may be accomplished by reacting the mandelate salts with a base such as an alkali or alkaline earth metal hydroxide, carbonate or bicarbonate (e.g., potassium hydroxide, magnesium hydroxide, sodium carbonate or sodium bicarbonate). Suitable solvents for the hydrolysis step include chlorohydrocarbons, ethers, benzene, toluene and water, as well as mixtures of the foregoing solvents (e.g., diethyl ether, diisopropyl ether, methylene chloride, or methylene chloride/water). Suitable temperatures range from about 15° C. to about 100° C., with room temperature being preferred.

The reaction of a compound of the formula IVA with a compound of the formula $R^1CHO$ to produce a compound of the formula VA is typically carried out in the presence of a reducing agent such as sodium cyanoborohydride, sodium triacetoxyborohydride, sodium borohydride, hydrogen and a metal catalyst, zinc and hydrochloric acid, or formic acid at a temperature from about −60° C. to about 50° C. Suitable reaction inert solvents for this reaction include lower alcohols (e.g, methanol, ethanol and isopropanol), acetic acid and THF. Preferably, the solvent is acetic acid, the temperature is about 25° C., and the reducing agent is sodium triacetoxyborohydride. This reaction proceeds to give material in which the addition of the $CH_2R^1$ sidechain occurs selectively at the 3-amino group, and the isomer of formula VA is the only product isolated.

Alternatively, the reaction of compound of the formula IVA with a compound of the formula $R^1CHO$ may be carried out in the presence of a drying agent or using an apparatus designed to remove azeotropically the water generated, to produce an imine of the formula

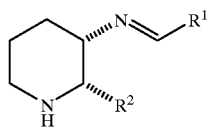

which is then reacted with a reducing agent as described above, preferably with sodium triacetoborohydride at about room temperature. The preparation of the imine is generally carried out in a reaction inert solvent such as benzene, toluene or xylenes, preferably toluene, at a temperature from about 25° C. to about 110° C., preferably at about the reflux temperature of the solvent. Suitable drying agents/solvent systems include titanium tetrachloride/dichloromethane and molecular sieves/THF. Titanium tetrachloride/dichloromethane is preferred.

The reaction of a compound of the formula IVA with a compound of the formula $R^1CH_2X$ is typically carried out in a reaction inert solvent such as dichloromethane or THF, preferably dichloromethane, at a temperature from about 0° C. to about 60° C., preferably at about 25° C.

The reaction of a compound of the formula IVA with a compound of the formula

is typically carried out in an inert solvent such as THF or dichloromethane at a temperature from about −20° C. to about 60° C., preferably in dichloromethane at about 25° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

Hydrogenation in the presence of a metal catalyst is the preferred method of reduction. Suitable hydrogenation catalysts include palladium, platinum, nickel and rhodium. The preferred catalyst for hydrogenation is platinum on carbon. The reaction temperature may range from about 10° C. to about 50° C., with about 25° C. being preferred. The hydrogenation is generally carried out at a pressure from about 1.5 to about 4 atmospheres, preferably at about 3.0 atmospheres.

The starting materials of the formulae

$R^1CHO$ and $R^1CH_2X$ are either commercially available or obtainable by carrying out standard transformation well known to those skilled in the art upon commercially available materials. Table 1 below indicates how the aldehydes of the formula $R^1CHO$ used in the examples were obtained. The standard transformations used to prepare these aldehydes are identified by one or more lower case letters in the column labelled "Reaction Sequence" in Table 1. The letters used to identify such transformations are explained in the key following Table1 1.

TABLE 1

Preparation of $R^1CHO$

| $R^1$ | Starting Material | Reaction Sequence* |
|---|---|---|
| 2,5-dimethoxyphenyl | — | commercial |
| 4,5-difluoro-2-methoxyphenyl | 3,4-difluoro-methoxybenzene | a |
| 2-chloro-5-fluorophenyl | — | commercial |
| 2-ethoxyphenyl | — | commercial |
| 2-hydroxyphenyl | — | commercial |
| 3,5-difluoro-2-methoxyphenyl | 2,4-difluoro-methoxybenzene | a |
| 2-chloro-6-fluorophenyl | — | commercial |
| 5-chloro-2-methoxyphenyl | 4-chloro-methoxybenzene | a |
| 3-fluoro-2-methoxyphenyl | 3-fluoro-2-hydroxybenzaldehyde | b |
| 5-chloro-3-fluoro-2-methoxyphenyl | 4-chloro-2-fluorophenol | b, a |
| 3-chloro-5-fluoro-2-methoxyphenyl | 2-chloro-4-fluoro-methoxybenzene | a |
| 3,5-dichloro-2-methoxyphenyl | 2,4-dichloro-methoxybenzene | a |
| 4-methoxyphenyl | — | commercial |
| 2-thienyl | — | commercial |
| 2-methoxynaphthyl | — | commercial |
| 3-thienyl | — | commercial |
| 2,5-difluorophenyl | — | commercial |
| 2,4-dimethoxyphenyl | — | commercial |
| 2,4-dichloro-6-methoxyphenyl | 3,5-dichloro-methoxybenzene | a |
| 2,6-dichloro-4-methoxyphenyl | 3,5-dichloro-methoxybenzene | a |
| 3,4-dichloro-2-methoxyphenyl | 2,3-dichloro-methoxybenzene | a |
| 2,3-dimethoxyphenyl | — | commercial |
| 5-bromo-2-methoxy-3-methylphenyl | 2-methyl-methoxybenzene | c, a |
| 2-cyclopentyloxyphenyl | 2-hydroxybenzaldehyde | d |
| 2-cyclopentyloxy-5-methoxyphenyl | 2-hydroxy-5-methoxybenzaldehyde | d |
| 5-t-butyl-2-methoxyphenyl | 4-t-butylphenol | e, a |
| 5-s-butyl-2-methoxyphenyl | 4-s-butylphenol | a |
| 5-fluoro-2-methoxyphenyl | 4-fluoro-methoxybenzene | f |

TABLE 1-continued

Preparation of R¹CHO

| R¹ | Starting Material | Reaction Sequence* |
|---|---|---|
| 2-acetamidophenyl | 2-aminobenzaldehyde | commercial |
| 2-methoxyphenyl | — | a |
| 5-isopropyl-2-methoxyphenyl | 4-isopropyl-methoxybenzene | e, a |
| 5-n-propyl-2-methoxyphenyl | 4-n-propylphenol | e, a |
| 4,5-dimethyl-2-methoxyphenyl | 3,4-dimethylphenol | e, a |
| 5-heptyl-2-methoxyphenyl | 4-heptylphenol | e, a |
| 2-heptyloxy-5-methoxyphenyl | 4-heptyloxyphenol | e, a |
| 5-heptyloxy-2-methoxyphenyl | 4-heptyloxyphenol | g, h |
| 2-(2,2,2-trifluoroethoxy)phenyl | 2-chlorobenzonitrile | i |
| quinolin-8-yl | 8-methylquinoline | a |
| 5-hydroxy-2-methoxyphenyl | 4-methoxyphenol | e, a |
| 2-methoxy-5-phenylphenyl | 4-phenylphenol | j |
| 4-amino-5-chloro-2-methoxyphenyl | 4-amino-5-chloro-2-methoxybenzoic acid | k |
| 2-hydroxy-5-trifluoromethoxyphenyl | 2-methoxy-5-trifluoromethoxybenzaldehyde | a |
| 5-t-butyl-2-hydroxyphenyl | 4-t-butylphenol | commercial |
| 3-trifluoromethoxyphenyf | — | g, h |
| 5-chloro-2-(2,2,2-trifluoroethoxy)phenyl | 2,6-dichlorobenzonitrile | e |
| 5-carbomethoxy-2-methoxyphenyl | 5-carbomethoxy-2-hydroxybenzaldehyde | l, m |
| 5-t-butyl-2-trifluoromethoxyphenyl | trifluoromethoxybenzene | e, a |
| 5-n-butyl-2-methoxyphenyl | 4-n-butyfphenol | n, a |
| 2-ethoxy-5-trifluoromethoxyphenyl | 4-trifluoromethoxyphenol | e, a |
| 2-methoxy-5-phenoxyphenyl | 4-phenoxyphenol | a |
| 5-ethyl-2-methoxyphenyl | 4-ethyl-methoxybenzene | p |
| 2-difluoromethoxy-5-trifluoromethoxyphenyl | 2-hydroxy-5-trifluoromethoxybenzaldehyde | g, a |
| 5-isopropyl-2-(2,2,2-trifluoroethoxy)phenyl | 4-isopropyl-iodobenzene | q, a |
| 2-isopropoxy-5-trifluoromethoxyphenyl | 4-trifluoromethoxyphenol | e, r |
| 5-dimethylamino-2-methoxyphenyl | 5-amino-2-hydroxybenzaldehyde | |
| 5-t-butyl-2-difluoromethoxyphenyl | 4-t-butylphenol | a, p |
| 2-methoxy-5-(N-methylsulfonamido)phenyl | 5-amino-2-hydroxybenzoic acid | s |
| 5-methylmercapto-2-methoxyphenyl | 4-methylthiophenol | e, a |
| 2-methoxy-5-methylaminomethylphenyl | 2-methoxy-5-(N-methylcarboxamido)benzaldehyde | t |
| 2-methoxy-5-methylsulfoxyphenyl | 5-methylmercapto-2-methoxybenzaldehyde | u |
| 2-methoxy-5-methylsulfonylphenyl | 5-methylmercapto-2-methoxybenzaldehyde | u |
| 2,5-bis(difluoromethoxy)phenyl | 2,5-dihydrobenzaldehyde | p |
| 2-difluoromethoxy-5-dimethylaminophenyl | 5-amino-2-hydroxybenzaldehyde | r, p |
| 2-difluoromethoxy-5-isopropylphenyl | 4-isopropylphenol | a, p |
| 2-difluoromethoxy-5-methylthiophenyl | 4-methylthiophenol | e, m, k, p |
| 2-difluoromethoxy-5-nitrophenyl | 2-hydroxy-5-nitrobenzaldehyde | p |
| 5-dimethylamino-2-(2,2,2-trifluoroethoxy)phenyl | 2-chloro-5-nitrobenzonitrile | g, r, h |
| 5-acetamido-2-(2,2,2-trifluoroethoxy)phenyl | 5-nitro-2-(2,2,2-trifluoroethoxy)benzonitrile | v, f, h |
| 2-difluoromethoxy-5-ethylphenyl | 4-ethyl-methoxybenzene | a, k, p |
| 5-chloro-2-difluoromethoxyphenyl | 5-chloro-2-hydroxybenzaldehyde | p |
| 2-trifluoromethoxyphenyl | — | commercial |
| 2-methoxy-5-trifluoromethoxyphenyl | 4-trifluoromethoxyphenol | e, a |

*Reagents for Preparation of R¹CHO From Standard Routes
a Cl$_2$CHOCH$_3$,TiCl$_4$
b dimethylsulfate
c Br$_2$/HOAc

TABLE 1-continued

Preparation of $R^1CHO$

| $R^1$ | Starting Material | Reaction Sequence* |
|---|---|---| d cyclopentyl bromide
e methyl iodide
f acetyl chloride
g $NaOCH_2CF_3$
h Raney nickel, $HCO_2H$
i $SeO_2$
j 1) carbonyldiimidazole, 2) N,O-dimethylhydroxylamine, 3) diisolbutylaluminum hydride
k $BBr_3$
l t-butyl chloride/$AlCl_3$
m $Cl_2CHOCH_3$/$AlCl_3$
n ethyl iodide
p $ClF_2CH$
q isopropyl bromide
r $H_2$, Pd/C, HCHO
s 1) methanol/HCl, 2) methylsulfonyl chloride, 3) methyl iodide, 4) diisobutylauminum hydride, 5) $MnO_2$
t borane methylsulfide complex
u monoperoxyphthalic acid, magnesium salt hexahydrate
v $H_2$—Pd/$BaSO_4$ The preparation of other compounds of the formula V not specifically described in the foregoing experimental section can be accomplished using combinations of the reactions described above that will be apparent to those skilled in the art.

In each of the reactions discussed or illustrated in schemes 1 to 3 above, pressure is not critical unless otherwise indicated. Pressures from about 0.5 atmospheres to about 5 atmospheres are generally acceptable, and ambient pressure, i.e. about 1 atmosphere, is preferred as a matter of convenience.

Compounds of the formula V and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of formula V which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of formula V which are also acidic in nature, e.g., where $R^6$ or $R^{10}$ is carboxyphenyl, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of formula V and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, urinary incontinence, gastrointestinal disorders such as emesis, colitis and Crohn's disease, psychosis, pain, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of formula V and their pharmaceutically acceptable salts can be administered via either the oral, parenteral or topical routes. In general, these compounds are most desirably administered in dosages ranging from about 5.0 mg up to about 1500 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its Individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of formula V and their pharmaceutically acceptable salts may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutic compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the formula V, or a pharmaceutically acceptable salt thereof, in either sesame or peanut oil or in aqueous propylene glycol may be employed. The aqueous solutions should be suitably buffered if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of formula V, or pharmaceutically acceptable salts thereof, topically when treating inflammatory conditions of the skin and this may preferably be done by way of creams, jellies, gels, pastes, ointments and the like, in accordance with standard pharmaceutical practice.

The activity of compounds of the formula V and their pharmaceutically acceptable salts as substance P receptor antagonists may be determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 4 $\mu$g/ml of bacitracin, 4 $\mu$g/ml of leupeptin, 2 $\mu$g of chymostatin and 200 g/ml of bovine serum albumin. This step completes the production of the tissue preparation.

The radioligand binding procedure is then carried out in the following manner, viz., by initiating the reaction via the addition of 100 $\mu$l of the test compound made up to a concentration of 1 $\mu$M, followed by the addition of 100 $\mu$l of radioactive ligand made up to a final concentration 0.5 mM and then finally by the addition of 800 $\mu$l of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The ability of the therapeutic compounds of this invention to inhibit substance P induced effects in vivo may be determined by the following procedures "a" through "d". (Procedures "a" through "c" are described in Nagahisa et al., *European Journal of Pharmacology*, 217, 191–5 (1992), which is incorporated herein by reference in its entirety.)

a. Plasma Extravasation in the Skin

Plasma extravasation is induced by intradermal administration of substance P (50 $\mu$l, 0.01% BSA-saline solution) in dorsal skin of pentobarbital (25 mg/kg i.p.) anesthetized male Hartley guinea pigs weighing 450–500 g. The compound to be tested is dissolved in 0.1% methyl cellulose-water (MC) and dosed p.o. 1 hour before substance P challenge (3 pmol/site). Evans blue dye (30 mg/kg) is administered intravenously 5 minutes before challenge. After 10 minutes, the animals are sacrificed, the dorsal skin is removed, and the blue spots are punched out using a cork borer (11.5 mm oral dose (o.d.)). Tissue dye content is quantitated after overnight formamide extraction at 600 nm absorbance.

b. Capsaicin-induced Plasma Extravasation

Plasma extravasation is induced by intraperitoneal injection of capsaicin (10 ml of 30 $\mu$M solution in 0.1% BSA/saline) into pentobarbital anesthetized (25 mg/kg i.p.) guinea pigs. The compound to be tested is dissolved in 0.1% MC and dosed p.o. 1 hour before capsaicin challenge. Evans blue dye (30 mg/kg) is administered i.v. 5 minutes before challenge. After 10 minutes, the animals are sacrificed, and both right and left ureters are removed. Tissue dye content is quantitated as in "a" above.

c. Acetic Acid-induced Abdominal Stretching

Male ddY mice (SLC, Japan), weighing 14–18 g, were fasted overnight. The compound to be tested is dissolved in 0.1% MC and dosed p.o. 0.5 hour before acetic acid (AA) injection (0.7%, 0.16 ml/10 g body weight). The animals are placed in clear beakers (1 per beaker) and the stretching response is counted 10 to 20 minutes after the AA injection (10 minute interval).

d. Substance P-induced Hyperlocomotor Paradigm

The anti-psychotic activity of the therapeutic compounds of the present invention as neuroleptic agents for the control of various psychotic disorders may be determined by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

(+)-(2S,3S)-3-(2-Methoxybenzylamino)-2-phenylpiperidine hydrochloride

A. 3-Amino-2-phenylpiperidine

A 500 ml Parr bottle was charged with 5 grams of 5% platinum/carbon (50% water wet), 5 grams (0.0293 mol.) 3-amino-2-phenylpyridine (1 equivalent), 75 ml of water (15 vol.) and 25 ml of concentrated hydrochloric acid (5 vol.). The reaction was hydrogenated (maintaining the hydrogen pressure between 36 psi and 50 psi) until high pressure liquid chromatography (HPLC) indicated complete reaction. The catalyst was removed by filtration and the pH of the filtrate was adjusted from 0 to a stable 11.2 using 25% sodium hydroxide (NaOH). The aqueous layer was extracted twice with 50 ml of methylene chloride ($CH_2Cl_2$). The organic extracts were combined, dried with magnesium sulfate ($MgSO_4$) and the filtrate was atmospherically distilled to an oil, 4.34 grams (84.1%).

B. (+)-(2S,3S)-3-Amino-2-phenylpiperidine mandelate salt

A magnetically stirred 500 ml erlenmeyer flask was charged with 373 ml acetonitrile ($CH_3CN$) (20 vol.), 10 grams (0.0567 mol.) 3-amino-2-phenylpiperdine (1 equivalent) and 8.63 grams (0.0567 mol.) L-(+)-mandelic acid. This clear amber solution started to precipitate within 15 minutes. The resulting slurry was granulated at ambient temperature for 2 hours, filtered, and the filter cake was washed with $CH_3CN$.

The wet solids were added to a paddle stirred 3 neck flask with 186 ml of $CH_3CN$ and heated to 82° C. for 1 hour. This slurry was allowed to cool to 24° C. over 90 minutes, after which solids were collected by filtration and washed with $CH_3CN$. The collected solids were vacuum dried at 45° C. for 18 hours, which afforded 6.9 grams of the (+)-(2S,3S)-3-amino-2-phenylpiperidine mandelate salt (74.2%).

Specific rotation $[\alpha]_D$=(+99.46°), c=1 ($CH_3OH$)

A magnetically stirred 500 ml flask was charged with 10 grams (0.03 mol.) 3-amino-2-phenylpiperidine mandelate salt and 200 ml of $CH_3CN$ (20 vol.). This slurry was heated to 82° C. for 1 hour, cooled to 24° C. over 1.5 hours and filtered. The filter cake was washed with $CH_3CN$ and vacuum dried at 45° C. to afford 8.63 grams (86.3%).

Specific rotation $[\alpha]_D$=(+107.92°), c=1 ($CH_3OH$).

The solids were charged to a magnetically stirred 500 ml flask which contained 176 ml of $CH_3CN$. This slurry was heated to 82° C. for 1.5 hours and then allowed to cool to 24° C. over 2 hours. Solids were collected by filtration and washed with $CH_3CN$. After vacuum drying at 45° C. for 18 hours, 7.66 grams of the 3-amino-2-phenylpiperidine mandelate salt were obtained (88.7%). The total recovery of the title compound was 76.6%. Specific rotation $[\alpha]_D$=(+116.96°) c=1 ($CH_3OH$).

C. (+)-(2S,3S)-3-Amino-2-phenylpiperidine

A magnetically stirred 1L erlenmeyer flask was charged with 20 grams (0.06 mol.) of the (+)-(2S,3S)-3-amino-2-phenylpiperidine mandelate salt (1 equivalent), 200 ml $CH_2Cl_2$ (10 vol.) and 200 ml of water (10 vol.). The pH of this slurry was adjusted from 5.1 to a stable 12 with 25% NaOH. The layers were separated and the aqueous layer was extracted once with 200 ml of $CH_2Cl_2$. The combined organic extracts were treated with 1 gram (5% by wt.) of Darco® G-60 for 15 minutes then dried with $MgSO_4$ for 30 minutes. The Darco® and $MgSO_4$ were removed by filtration and the filtrate was concentrated atmospherically to yield 7.36 grams of the title compound. Oil, 67.8% yield.

Specific rotation $[\alpha]_D$=(+62.38°), c=1 ($CH_3OH$).

D. (+)-(2S,3S)-3-(2-Methoxybenzylamino)-2-phenylpiperidine

A magnetically stirred 100 ml flask was charged (under a nitrogen atmosphere) with 3 grams (0.017 mol.) of (+)-(2S,3S)-3-amino-2-phenylpiperidine (1 equivalent) and 30 ml of acetic acid (HOAc) (10 vol.). The reaction turned a raspberry color with addition of HOAc and then with continued stirring became slightly amber in color. The solution was stirred for 10 min., after which 2.54 g (0.0187 mol.) of 2-methoxybenzaldehyde (1.1 equivalents) was added, followed by the portionwise addition of 6.3 g (0.0297 mol.) of sodium triacetoxyborohydride (STAB) (1.75 equivalents). The reaction exothermed to 33° C. during the addition. The colorless solution was stirred for 18 hours at ambient temperature. The reaction became a solution within 30 minutes of the last addition of STAB. The reaction was concentrated under vacuum to an oil which was partitioned between 30 ml of $CH_2Cl_2$ and 30 ml of $H_2O$. The pH was adjusted from 4.0 to a stable 11.5 with 50% NaOH. After layer separation, the aqueous layer was extracted once with 30 ml of $CH_2Cl_2$. The aqueous layer was diluted with more water to dissolve waxy solids that formed. The combined organic layers were dried with $MgSO_4$ and filtered. The filtrate was concentrated atmospherically to yield an oil (4.86 g) which was dissolved in 20 ml of ethanol and charged to a 125 ml erlenmeyer flask and magnetically stirred. A solution of 40 ml ethanol and 2 grams of anhydrous hydrochloric acid (HCl) was added. The resulting slurry was granulated for 1 hour at 24° C. and then cooled to 5° C. for 1 hour. Solids were collected by filtration and washed with 5° C. ethanol. Vacuum drying at 45° C. gave 5.09 grams (81.2%) of the title compound.

Specific rotation $[\alpha]_D$=(+70.88°), c=1 (CH$_3$OH).

EXAMPLE 2

(+)-(2S,3S)-3-(2-Methoxy-5-trifluoromethoxybenzylamino)-2-phenylpiperidine hydrochloride A magnetically stirred 65 ml flask was charged (under a nitrogen atmosphere) with 1.5 g (0.0085 mol.) (+)-(2S,3S)-3-amino-2-phenylpiperidine (1 equivalent) and 30 ml of HOAc (20 vol.). The reaction was a sticky raspberry colored mixture which became a solution with stirring. The reaction was stirred for 15 minutes and 2.24 grams (0.0102 mol.) of 2-methoxy-5-trifluoromethoxybenzaldehyde (1.2 equivalents) was added, followed by the portionwise addition of 3.96 grams (0.0187 mol.) STAB (2.2 equivalents). The reaction exothermed to 33° C. during addition. This slightly pink solution was stirred at ambient for 18 hours. The reaction became a solution within 30 minutes of the last addition of STAB. The reaction was concentrated under vacuum to an oil and partitioned between 30 ml of CH$_2$Cl$_2$ and 30 ml of water. The pH was adjusted from 4.1 to a stable 11.9 with 50% NaOH. The layers were separated and the aqueous layer was extracted once with 30 ml of CH$_2$Cl$_2$. The combined organic layers were dried with MgSO$_4$ and filtered. The filtrate was concentrated atmospherically to yield an oil (3.56 grams) which was dissolved in 20 ml of ethanol (5.6 vol.), charged to a 125 ml erlenmeyer flask and magnetically stirred. A solution of 20 ml of ethanol and 2 grams anhydrous HCl was added and the resulting slurry was granulated for 1 hour at 24° C. and cooled to 5° C. for 1 hour. Solids were collected by filtration and washed with 5° C. ethanol. Vacuum drying at 40° C. afforded 2.85 grams of the title compound.

Specific rotation $[\alpha]_D$=(+69.84°), c=1 (CH$_3$OH).

Chiral HPLC (high pressure liquid chromatography) indicated that the product contained 1.64% of the opposite enantiomer.

Twenty grams of the title compound was combined with 40 ml of ethanol in a 60 ml flask. This suspension was magnetically stirred at reflux for 1.5 hours. After cooling to room temperature for over one hour, the suspension was filtered. The filter cake was washed with ethanol and dried in vacuo at 45° C. to afford 1.71 grams (85.5% recovery) of the chirally enriched title compound, which was shown by chiral HPLC to contain 0.16% of the opposite enantiomer.

Specific rotation $[\alpha]_D$=(+71.06°), c=1 (CH$_3$OH).

EXAMPLE 3

(−)-(2R,3R)-3-Amino-2-phenylpiperidine mandelate salt

3-Amino-2-phenylpiperidine was resolved according to the procedure described in the first two paragraphs of Example 1B (i.e., the additional purification steps were not performed), but substituting D-(−)-mandelic acid for L-(+)-mandelic acid and substituting methyl ethyl ketone for acetonitrile.

Specific rotation $[\alpha]_D$=(−92.27), c=1 (CH$_3$OH).

EXAMPLE 4

(+)-(2S,3S)-3-Amino-2-phenylpiperidine mandelate salt

3-Amino-2-phenylpiperidine was resolved according to the procedure described in the first two paragraphs of Example 1B (i.e., the additional purification steps were not performed), but substituting isopropyl alcohol for acetonitrile.

Specific rotation $[\alpha]_D$=(+45.71), c=1 (CH$_3$OH).

EXAMPLE 5

(+)-(2S,3S)-3-Amino-2-phenylpiperidine mandelate salt

3-Amino-2-phenylpiperidine was resolved according to the procedure described in the first two paragraphs of Example 1B (i.e., the additional purification steps were not performed), but substituting ethyl acetate for acetonitrile.

Specific rotation $[\alpha]_D$=(+112.23), c=1 (CH$_3$OH).

EXAMPLE 4

(+)-(2S,3S)-3-Amino2-phenylpiperidine mandelate salt

3-Amino-2-phenylpiperidine was resolved according to the procedure of Example 1B, but substituting isopropyl alcohol for acetonitrile.

Specific rotation $[\alpha]_D$=(+45.71), c=1 (CH$_3$OH).

EXAMPLE 5

(+)-(2S,3S)-3-Amino-2-phenylpiperidine mandelate salt

3-Amino-2-phenylpiperidine was resolved according to the procedure of Example 1B, but substituting ethyl acetate for acetonitrile.

Specific rotation $[\alpha]_D$=(+112.23), c=1 (CH$_3$OH).

What is claimed is:

1. A method of treating or preventing emesis in a mammal, comprising administering to said mammal an amount of a compound that is a substance P receptor antagonist, or a pharmaceutically acceptable salt thereof, that is effective in treating or preventing emesis.

2. A method of treating or preventing emesis in a mammal, comprising administering to said mammal a substance P receptor antagonizing effective amount of a compound of the formula

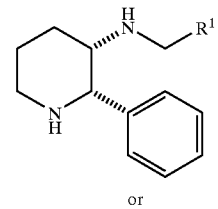

(VA)

or

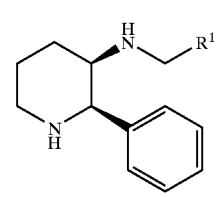

(VB)

wherein R$^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said (C$_3$–C$_7$) cycloalkyl may optionally be substituted with one or two substituents, said substituents being independently selected from chloro, fluoro, bromo, iodo, nitro, $(C_1-C_{10})$ alkyl optionally substituted from one to three fluoro groups, $(C_1-C_{10})$ alkoxy optionally substituted with from one to three fluoro groups, amino, $(C_1-C_{10})$alkyl-S—, $(C_1-C_{10})$alkyl-SO$_2$—, phenyl, phenoxy, $(C_1-C_{10})$alkyl-SO$_2$NH—, $(C_1-C_{10})$alkyl-SO$_2$NH—$(C_1-C_{10})$alkyl-, $(C_1-C_{10})$ alkylamino, cyano, hydroxy, cycloalkoxy having 3 to 7 carbon atoms, $(C_1-C_6)$dialkylamino, HC(=O)NH- and $(C_1-C_{10})$alkyl-C(=O)-NH;

or a pharmaceutically acceptable salt thereof, or a mixture of compounds of the formulae VA and VB or pharmaceutically acceptable salts of such compounds.

3. A method of treating or preventing emesis in a mammal, comprising administering to said mammal an amount of a compound of the formula

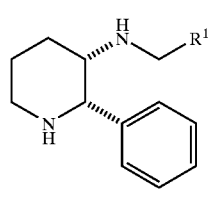

(VA)

or

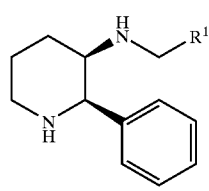

(VB)

wherein $R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, said substituents being independently selected from chloro, fluoro, bromo, iodo, nitro, $(C_1-C_{10})$ alkyl optionally substituted from one to three fluoro groups, $(C_1-C_{10})$ alkoxy optionally substituted with from one to three fluoro groups, amino,

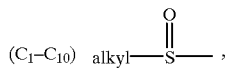

$(C_1-C_{10})$alkyl-S—, $(C_1-C_{10})$alkyl-SO$_2$—, phenyl, phenoxy, $(C_1-C_{10})$alkyl-SO$_2$NH—, $(C_1-C_{10})$alkyl-SO$_2$NH—$(C_1-C_{10})$alkyl-, $(C_1-C_{10})$alkylamino, cyano, hydroxy, cycloalkoxy having 3 to 7 carbon atoms, $(C_1-C_6)$ alkylamino, $(C_1-C_6)$dialkylamino, HC(=O)NH- and $(C_1-C_{10})$alkyl-C(=O)-NH;

or a pharmaceutically acceptable salt thereof, or a mixture of compounds of the formulae VA and VB or pharmaceutically acceptable salts of such compounds;

that is effective in treating or preventing emesis.

4. A method according to claim 2 or claim 3, wherein a compound of the formula VA or VB or a pharmaceutically acceptable salt of such compound is administered, in which $R^1$ is selected from:

2,5-dimethoxyphenyl; 4,5-difluoro-2-methoxyphenyl; 2-chloro-5-fluorophenyl; 2-ethoxyphenyl; 2-hydroxyphenyl; 3,5-difluoro-2-methoxyphenyl; 2-chloro-6-fluorophenyl; 5-chloro-2-methoxyphenyl; 3-fluoro-2-methoxyphenyl; 5-chloro-3-fluoro-2-methoxyphenyl; 3-chloro-5-fluoro-2-methoxyphenyl; 3,5-dichloro-2-methoxyphenyl; 4-methoxyphenyl; 2-thienyl; 2-methoxynaphthyl; 3-thienyl; 2,5-difluorophenyl; 2,4-dimethoxyphenyl; 2,4-dichloro-6-methoxyphenyl; 2,6-dichloro-4-methoxyphenyl; 3,4-dichloro-2-methoxyphenyl; 2,3-dimethoxyphenyl; 5-bromo-2-methoxy-3-methylphenyl; 2-cyclopentyloxyphenyl; 2-cyclopentyloxy-5-methoxyphenyl; 5-t-butyl-2-methoxyphenyl; 5-s-butyl-2-methoxyphenyl; 5-fluoro-2-methoxyphenyl; 2-acetamidophenyl; 2-methoxyphenyl; 5-isopropyl-2-methoxyphenyl; 5-n-propyl-2-methoxyphenyl; 4,5-dimethyl-2-methoxyphenyl; 5-heptyl-2-methoxyphenyl; 2-heptyloxy-5-methoxyphenyl; 5-heptyloxy-2-methoxyphenyl; 2-(2,2,2-trifluoroethoxy)phenyl; quinolin-8-yl; 5-hydroxy-2-methoxyphenyl; 2-methoxy-5-phenylphenyl; 4-amino-5-chloro-2-methoxyphenyl; 2-hydroxy-5-trifluoromethoxyphenyl; 5-t-butyl-2-hydroxyphenyl; 3-trifluoromethoxyphenyl; 5-chloro-2-(2,2,2-trifluoroethoxy)phenyl; 5-carbomethoxy-2-methoxyphenyl; 5-t-butyl-2-trifluoromethoxyphenyl; 5-n-butyl-2-methoxyphenyl; 2-ethoxy-5-trifluoromethoxyphenyl; 2-methoxy-5-phenoxyphenyl; 5-ethyl-2-methoxyphenyl; 2-difluoromethoxy-5-trifluoromethoxyphenyl; 5-isopropyl-2-(2,2,2-trifluoroethoxy)phenyl; 2-isopropoxy-5-trifluoromethoxyphenyl; 5-dimethylamino-2-methoxyphenyl; 5-t-butyl-2-difluoromethoxyphenyl; 2-methoxy-5-(N-methylsulfonamido)phenyl; 5-methylmercapto-2-methoxyphenyl; 2-methoxy-5-methylaminomethylphenyl; 2-methoxy-5-methylsulfoxyphenyl; 2-methoxy-5-methylsulfonylphenyl; 2,5-bis(difluoromethoxy) phenyl; 2-difluoromethoxy-5-dimethylaminophenyl; 2-difluoromethoxy-5-isopropylphenyl; 2-difluoromethoxy-5-methylthiophenyl; 2-difluoromethoxy-5-nitrophenyl; 5-dimethylamino-2-(2,2,2-trifluoroethoxy)phenyl; 5-acetamido-2-(2,2,2-trifluoroethoxy)phenyl; 2-difluoromethoxy-5-ethylphenyl; 5-chloro-2-difluoromethoxyphenyl; 2-trifluoromethoxyphenyl; and 2-methoxy-5-trifluoromethoxyphenyl.

5. A method according to claim 1 or 2, wherein a compound of the formula VA or VB or a pharmaceutically acceptable salt of such compound is administered, in which $R^1$ is selected from:

2,5-dimethoxyphenyl; 4,5-difluoro-2-methoxyphenyl; 2-chloro-5-fluorophenyl; 2-ethoxyphenyl; 2-hydroxyphenyl; 3,5-difluoro-2-methoxyphenyl; 2-chloro-6-fluorophenyl; 5-chloro-2-methoxyphenyl; 3-fluoro-2-methoxyphenyl; 5-chloro-3-fluoro-2-methoxyphenyl; 3-chloro-5-fluoro-2-methoxyphenyl; 3,5-dichloro-2-methoxyphenyl; 4-methoxyphenyl; 2-thienyl; 2-methoxynaphthyl; 3-thienyl; 2,5-difluorophenyl; 2,4-dimethoxyphenyl; 2,4-dichloro-6-methoxyphenyl; 2,6-dichloro-4-methoxyphenyl; 3,4-dichloro-2-methoxyphenyl; 2,3-dimethoxyphenyl; 5-bromo-2-methoxy-3-methylphenyl; 2-cyclopentyloxyphenyl; 2-cyclopentyloxy-5- methoxyphenyl; 5-t-butyl-2-methoxyphenyl; 5-s-butyl-2-methoxyphenyl; 5-fluoro-2-methoxyphenyl; 2-acetamidophenyl; 2-methoxyphenyl; 5-isopropyl-2-methoxyphenyl; 5-n-propyl-2-methoxyphenyl; 4,5-dimethyl-2-methoxyphenyl; 5-heptyl-2-methoxyphenyl; 2-heptyloxy-5-methoxyphenyl; 5-heptyloxy-2-methoxyphenyl; quinolin-8-yl; 5-hydroxy-2-methoxyphenyl; 2-methoxy-5-phenylphenyl; 4-amino-5-chloro-2-methoxyphenyl; 5-t-butyl-2-hydroxyphenyl; 5-carbomethoxy-2-methoxyphenyl; 5-n-butyl-2-methoxyphenyl; 2-methoxy-5-phenoxyphenyl; 5-ethyl-2-methoxyphenyl; 5-dimethylamino-2-methoxyphenyl; 2-methoxy-5-(N-methylsulfonamido)phenyl; 5-methylmercapto-2-methoxyphenyl; 2-methoxy-5-methylaminomethylphenyl; 2-methoxy-5-methylsulfoxyphenyl; and 2-methoxy-5-methylsulfonylphenyl.

6. A method according to claim 1, wherein a compound or salt of a compound of the formula VA or VB is administered, in which $R^1$ is either unsubstituted or substituted with a number of substituents, wherein such number is as defined in claim 1 and said substituents are selected from halo, nitro, $(C_1-C_6)$ alkyl, $(C_1-C_6)$ alkoxy, trifluoromethyl, amino, $(C_1-C_6)$ alkylamino, —CONH$(C_1-C_6)$ alkyl, $(C_1-C_6)$alkyl-CONH—$(C_1-C_6)$alkyl, —NHC(O)H and —NHC(O)—$(C_1-C_6)$alkyl.

7. A method according to claim 2, wherein a compound or salt of a compound of the formula VA or VB is administered, in which $R^1$ is either unsubstituted or substituted with a number of substituents, wherein such number is as defined in claim 1 and said substituents are selected from halo, nitro, $(C_1-C_6)$ alkyl, $(C_1-C_6)$ alkoxy, trifluoromethyl, amino, $(C_1-C_6)$ alkylamino, —CONH$(C_1-C_6)$alkyl, $(C_1-C_6)$alkyl-CONH—$(C_1-C_6)$alkyl, —NHC(O)H and —NHC(O)—$(C_1-C_6)$alkyl.

* * * * *